US007935099B2

(12) United States Patent
Sue et al.

(10) Patent No.: US 7,935,099 B2
(45) Date of Patent: May 3, 2011

(54) ABSORBENT ARTICLE WITH PATTERNED SBS BASED ADHESIVE

(75) Inventors: Shunketsu Sue, Mason, OH (US);
Ebrahim Rezai, Mason, OH (US);
Ravindra Palitha Ranatunga, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 123 days.

(21) Appl. No.: 11/717,975

(22) Filed: Mar. 14, 2007

(65) Prior Publication Data
US 2008/0228158 A1 Sep. 18, 2008

(51) Int. Cl.
*A61F 13/15* (2006.01)
*A61F 13/20* (2006.01)
*B29C 65/00* (2006.01)
*B31B 1/60* (2006.01)
*B32B 37/00* (2006.01)
*G05G 15/00* (2006.01)
*B65H 81/00* (2006.01)
*A61F 5/32* (2006.01)

(52) U.S. Cl. ........ 604/387; 604/358; 604/367; 604/372; 604/384; 604/385.01; 604/385.23; 604/385.24; 156/60; 156/349; 156/425; 128/846

(58) Field of Classification Search .................. 604/358, 604/367, 372, 384, 385.01, 385.23, 385.24; 156/60, 349, 425; 128/846
See application file for complete search history.

(56) References Cited

U.S. PATENT DOCUMENTS

| 3,848,594 | A |   | 11/1974 | Buell |
|---|---|---|---|---|
| 3,860,003 | A |   | 1/1975 | Buell |
| 3,911,173 | A | * | 10/1975 | Sprague, Jr. ............... 427/208.6 |
| 4,104,327 | A | * | 8/1978 | Inoue et al. ................... 524/505 |
| 4,125,665 | A | * | 11/1978 | Bemmels et al. ............. 428/352 |
| 4,526,577 | A |   | 7/1985 | Schmidt, Jr. et al. |
| 4,610,678 | A |   | 9/1986 | Weisman et al. |
| 4,662,875 | A |   | 5/1987 | Hirotsu et al. |
| 4,673,402 | A |   | 6/1987 | Weisman et al. |
| 4,699,622 | A |   | 10/1987 | Toussant et al. |
| 4,785,996 | A | * | 11/1988 | Ziecker et al. ................ 239/298 |
| 4,808,178 | A |   | 2/1989 | Aziz et al. |

(Continued)

FOREIGN PATENT DOCUMENTS
WO    WO 95/16746 A1    6/1995

OTHER PUBLICATIONS

Mark A. Peters, Ph.D., Eastman Chemical Co., Kingsport, TN. "Adhesives Essentials: Strategies to Help Tape and Label Manufacturers Extend Block Copolymer Usage." Adhesives and Sealants Industry Magazine. Jun. 1, 2005. Accessed Sep. 11, 2008. http://www.adhesivesmag.com/CDA/Archives/b85c006dffac8010VgnVCM100000f932a8c0.*

(Continued)

*Primary Examiner* — Tatyana Zalukaeva
*Assistant Examiner* — Adam Marcetich
(74) *Attorney, Agent, or Firm* — John G. Powell

(57) ABSTRACT

An SBS based construction adhesive that includes an amount of SIS adhesive to make an SBS/SIS adhesive that shows excellent shear hang time values when used to manufacture disposable absorbent articles. The SBS/SIS adhesive is applied in a spiral pattern having a particular width and frequency to form an endflap seal that may reduce the likelihood of a gel on skin occurrence.

15 Claims, 5 Drawing Sheets

U.S. PATENT DOCUMENTS

| | | | |
|---|---|---|---|
| 4,834,735 A | | 5/1989 | Alemany et al. |
| 4,846,815 A | | 7/1989 | Scripps |
| 4,880,420 A | * | 11/1989 | Pomparelli ............... 604/385.27 |
| 4,888,231 A | * | 12/1989 | Angstadt ........................ 428/213 |
| 4,894,060 A | | 1/1990 | Nestegard |
| 4,909,803 A | | 3/1990 | Aziz et al. |
| 4,940,464 A | | 7/1990 | Van Gompel et al. |
| 4,946,527 A | | 8/1990 | Battrell |
| 4,963,140 A | | 10/1990 | Robertson et al. |
| 5,024,667 A | * | 6/1991 | Malcolm et al. ............... 604/382 |
| 5,061,259 A | | 10/1991 | Goldman et al. |
| 5,092,861 A | | 3/1992 | Nomura et al. |
| 5,137,537 A | | 8/1992 | Herron et al. |
| 5,147,345 A | | 9/1992 | Young et al. |
| 5,149,741 A | * | 9/1992 | Alper et al. ....................... 525/95 |
| 5,151,092 A | | 9/1992 | Buell et al. |
| 5,160,746 A | * | 11/1992 | Dodge et al. ........................ 425/7 |
| 5,221,274 A | | 6/1993 | Buell et al. |
| 5,242,436 A | | 9/1993 | Weil et al. |
| 5,246,433 A | | 9/1993 | Hasse et al. |
| 5,260,345 A | | 11/1993 | DesMarais et al. |
| 5,342,338 A | | 8/1994 | Roe |
| 5,387,207 A | | 2/1995 | Dyer et al. |
| 5,397,316 A | | 3/1995 | LaVon et al. |
| 5,444,121 A | * | 8/1995 | Grennes et al. .................. 525/89 |
| 5,499,978 A | | 3/1996 | Buell et al. |
| 5,507,736 A | | 4/1996 | Clear et al. |
| 5,554,145 A | | 9/1996 | Roe et al. |
| 5,560,878 A | * | 10/1996 | Dragoo et al. ................. 264/115 |
| 5,569,234 A | | 10/1996 | Buell et al. |
| 5,571,096 A | | 11/1996 | Dobrin et al. |
| 5,580,411 A | | 12/1996 | Nease et al. |
| 5,583,182 A | * | 12/1996 | Asahara et al. ............... 525/314 |
| 5,591,152 A | | 1/1997 | Buell et al. |
| 5,601,542 A | * | 2/1997 | Melius et al. ................. 604/368 |
| 5,607,760 A | | 3/1997 | Roe |
| 5,609,587 A | | 3/1997 | Roe |
| 5,625,222 A | | 4/1997 | Yoneda et al. |
| 5,635,191 A | | 6/1997 | Roe et al. |
| 5,643,588 A | | 7/1997 | Roe et al. |
| 5,669,894 A | | 9/1997 | Goldman et al. |
| 5,728,219 A | * | 3/1998 | Allen et al. ..................... 118/315 |
| 5,762,642 A | * | 6/1998 | Coles et al. ..................... 604/378 |
| 5,865,823 A | | 2/1999 | Curro |
| 5,897,545 A | | 4/1999 | Kline et al. |
| 5,938,648 A | * | 8/1999 | LaVon et al. ................... 604/358 |
| 5,957,908 A | | 9/1999 | Kline et al. |
| 5,980,500 A | * | 11/1999 | Shimizu et al. .......... 604/385.01 |
| 6,004,306 A | | 12/1999 | Robles et al. |
| 6,107,537 A | | 8/2000 | Elder et al. |
| 6,120,487 A | | 9/2000 | Ashton |
| 6,120,489 A | | 9/2000 | Johnson et al. |
| 6,184,285 B1 | * | 2/2001 | Hatfield et al. ................ 524/505 |
| 6,197,012 B1 | * | 3/2001 | Mishima et al. .......... 604/385.04 |
| 6,232,391 B1 | | 5/2001 | Sambasivam et al. |
| 6,432,098 B1 | | 8/2002 | Kline et al. |
| 6,706,943 B2 | * | 3/2004 | Onishi et al. ................... 604/366 |
| 7,013,941 B2 | | 3/2006 | Schneider et al. |
| 7,473,817 B1 | * | 1/2009 | Tanaka et al. .................. 604/358 |
| 2004/0018223 A1 | * | 1/2004 | Chen ............................... 424/439 |
| 2004/0116591 A1 | * | 6/2004 | Chen ............................... 524/575 |
| 2004/0162536 A1 | | 8/2004 | Becker et al. |
| 2004/0167486 A1 | | 8/2004 | Busam et al. |
| 2005/0136773 A1 | * | 6/2005 | Yahiaoui et al. ............... 442/394 |
| 2005/0137549 A1 | * | 6/2005 | Lindsay et al. ........... 604/385.01 |
| 2005/0177123 A1 | | 8/2005 | Catalan |
| 2006/0135694 A1 | * | 6/2006 | Vaughan et al. ................. 525/88 |
| 2006/0155253 A1 | | 7/2006 | Dziezok et al. |
| 2006/0155254 A1 | | 7/2006 | Sanz et al. |
| 2006/0184146 A1 | * | 8/2006 | Suzuki ........................... 604/358 |
| 2006/0184151 A1 | * | 8/2006 | Onishi et al. .............. 604/385.19 |
| 2006/0264862 A1 | * | 11/2006 | Yoshida et al. ................ 604/386 |
| 2007/0055211 A1 | | 3/2007 | Shunketsu et al. |
| 2007/0088116 A1 | * | 4/2007 | Abba et al. ..................... 524/500 |
| 2007/0282287 A1 | * | 12/2007 | Noda et al. ................ 604/385.16 |

OTHER PUBLICATIONS

F. L. Buchholz and A.T. Graham, *Modern Super Absorbent Technology*, published by Wiley VCH, New York, 1998.

* cited by examiner

ABSORBENT ARTICLE WITH PATTERNED SBS BASED ADHESIVE

FIELD OF INVENTION

This invention relates generally to absorbent articles assembled using an SBS based adhesive that provides improved bonding strength and reduced odor. In particular, this invention relates to absorbent articles that reduce gel on skin.

BACKGROUND OF THE INVENTION

Users, for example caregivers of infants, rely on disposable absorbent articles to make their lives easier. Disposable absorbent articles, such as adult incontinence articles and diapers, are generally manufactured by combining several components. These components may include a liquid-permeable topsheet, a liquid-impermeable backsheet attached to the topsheet, and an absorbent core located between the topsheet and the backsheet. When the disposable article is worn, the liquid-permeable topsheet is typically positioned next to the body of the wearer. The topsheet is often configured to allow passage of bodily fluids into the absorbent core. The liquid-impermeable backsheet may help prevent leakage of fluids held in the absorbent core. The absorbent core generally is designed to have desirable physical properties, e.g. a high absorbent capacity and high absorption rate, so that bodily fluids can be transported into the disposable absorbent article. One way to provide a core with a desirable absorbent capacity and/or high absorption rate is to construct the core from an absorbent material, such as, for example cellulose fiber (commonly referred to as airfelt in the art) or superabsorbent polymer ("SAP") particles.

Frequently one or more components of a disposable absorbent article are adhesively bonded together. For example, adhesives have been used to bond individual layers of the absorbent article, such as the topsheet and the backsheet together. Adhesives have also been used to bond discrete components, such as fasteners and leg elastics or cuffs, to each other or to the article. Such adhesives are often referred to as construction adhesives because they are used to help construct the absorbent article from individual components. In many instances, a hot-melt adhesive, i.e. a polymeric formulation that is heated in order to substantially liquefy the formulation prior to application to one or more materials, is used as a construction adhesive.

In order to achieve a desirable level and/or rate of liquid absorption, many disposable absorbent articles include SAP particles. While the SAP particles may be suitable for such a purpose, one or more of the particles may become separated from the article and adhere to the skin of the user. SAP particles that become separated from a disposable absorbent article and adhere to the skin of a user or wearer of the disposable absorbent article may create a condition commonly referred to as gel on skin. Gel on skin is considered undesirable by many consumers. One way manufacturers may attempt to reduce gel on skin is to modify the amount of adhesive applied to particular area of the absorbent article, such as, for example by substantially covering most, if not all, of a particular surface area of a substrate with adhesive, and bonding portions of two or more substrates to one another with the adhesive to form a seal. The portions of the substrates that form the seal may also define a substantially enclosed area for containing most, if not all, of the SAP particles within the disposable absorbent article. One example of a commonly known method for substantially coating an entire area of a substrate is slot coating. Unfortunately, coating methods such as slot coating may result in unnecessarily higher manufacturing costs if the manufacturer is applying more adhesive than is actually needed to construct the article.

In addition to potentially higher manufacturing costs, when an entire area of a disposable absorbent article is substantially covered with adhesive, other issues may arise. One such issue may be the catastrophic failure of the bonded material during manufacturing due to a lack of escape routes for air that may be trapped in the disposable absorbent article. For example, if the topsheet and backsheet of a disposable diaper are joined or sealed around the perimeter of the diaper such that a relatively air tight space is defined between the topsheet and backsheet, then a pocket of air may form within the diaper. Subsequently, when the diaper is subjected to mechanical stress, such as, for example a nip or calendar roll, the adhesive bond may fail due to the pressure of the trapped air being applied to a particular portion of the disposable absorbent article. Once the diaper material or the seal fails, the resulting opening may provide a way for the SAP particles to escape the diaper core.

Another problem of applying enough adhesive to substantially coat an entire surface is the creation of detectable odors. Some adhesives are made of chemicals that may produce odors, which are detectable by consumers. Consumers may consider these odors to be undesirable, and some consumers may even consider the odors to indicate the presence of an unsafe substance. As a result, manufacturers may wish to minimize the amount of adhesive applied to a disposable absorbent article for reasons other than cost.

In order to address the problems of excessive adhesive application, some manufacturers may apply adhesive in an intermittent pattern, such as, for example parallel lines (e.g., beads of adhesive that are substantially parallel to one another). In such a configuration, areas having little or no adhesive (often referred to as channels) may be formed between the lines of adhesive, and any trapped air in the disposable absorbent article may pass through the channels to the outside of the diaper. Thus, by allowing any trapped air to exit the diaper via the channels, the likelihood of a material and/or seal failure due to excessive air pressure buildup may be reduced. However, one problem with providing channels in a disposable absorbent article is that the channels may also provide a way for the SAP particles to escape from the disposable absorbent article. Also, if the beads of adhesive are too narrow, then there may be insufficient bond strength or too low of an open time (i.e., the time when a hot melt adhesive is at a high enough temperature to join components together). In order to narrow the width of the channels or increase the bond strength, the adhesive bead can be made wider. Although if the adhesive bead is too wide, the open time may become too high, thereby increasing the chance of a hygiene issue on the production line.

Accordingly, it would be desirable to provide a disposable absorbent article that includes an adhesive with improved adhesive strength. It would also be desirable to provide a disposable absorbent article with an adhesive applied in a pattern that permits the escape of air but not the escape of SAP particles. It would even further be desirable to provide a disposable absorbent article with an adhesive having reduced odor.

SUMMARY OF THE INVENTION

In order to provide a solution to the problems set forth above, one embodiment of the present invention provides a disposable absorbent article having a pair of opposing end edges and a pair of longitudinal side edges. The disposable absorbent article also includes a topsheet, a backsheet and an absorbent core disposed between the topsheet and backsheet. The absorbent core includes SAP particles. The disposable absorbent article also has a garment facing side, an opposing wearer facing side, and an SBS/SIS adhesive disposed on a portion of the disposable absorbent article in a spiral pattern. The SBS/SIS adhesive joins at least a first portion of the disposable absorbent article to a second portion of the disposable absorbent article by an adhesive bond. The adhesive bond has a shear hang time of greater than about 40 seconds as measured according to the Shear Hang Time Test.

DETAILED DESCRIPTION OF THE INVENTION

Figure 1:
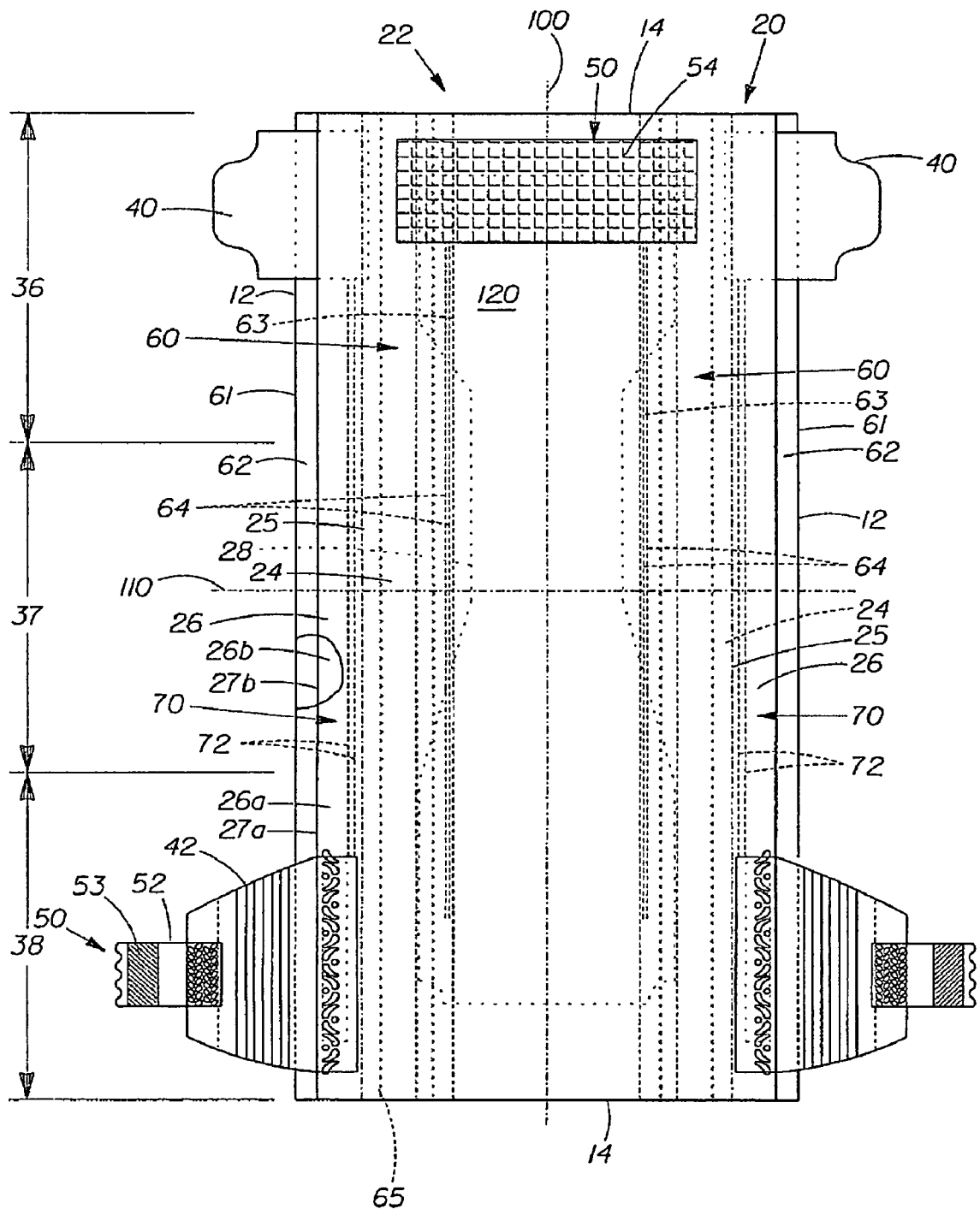
FIG. 1 is a plan view of a disposable absorbent article in a flat, uncontracted state.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as the diaper illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal".

"Lateral" refers to a direction running from a longitudinal edge to an opposing longitudinal edge of the article and generally at a right angle to the longitudinal direction. Directions within 45 degrees of the lateral direction are considered to be "lateral."

"Orthogonal" refers to a direction that is generally at a right angle to another direction. Directions within 45 degrees of the other direction are considered to be orthogonal.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s), which in turn are affixed to the other element.

As used herein the term "permanent bond" generally refers to the attachment of two or more elements or portions of elements together in a manner in which they are not intended to be separated during normal use of the article. Separation of such a permanent bond results in degradation of the attachment and/or of portions of the article. The performance of the article for its intended use is compromised upon breaking of a permanent bond.

The term "construction adhesive" as used herein generally refers to an adhesive used to join one or more components of a disposable absorbent article to themselves or together during the manufacturing process. The adhesive bond formed by a construction adhesive is typically intended to be a permanent bond, but need not necessarily be so.

"Film" refers to a sheet-like material wherein the length and width of the material far exceed the thickness of the material. Typically, films have a thickness of about 0.5 mm or less.

As used herein, the term "spiral" refers to a shape or pattern that generally resembles a helix as viewed in a two dimensional plane from a direction substantially orthogonal to the helix's axis of rotation, as exemplified in the figures.

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Unless otherwise noted, "Laminated structure" or "laminate" means a structure in which one layer, material, component, web, or substrate is adhesively bonded, at least in part, to another layer, material, component, web, or substrate. As stated elsewhere in this application, a layer, material, component, web, or substrate may be folded over and adhesively bonded to itself to form a "laminated structure" or "laminate."

It is to be understood that while particular examples recited herein may refer to a diaper, the present invention is not limited to diapers. The present invention may, in fact, be practiced to great advantage in any situation where a disposable absorbent article exhibiting the following described characteristics is required. It is believed the detailed description contained herein will allow one skilled in the art to readily adapt the invention to other applications.

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 includes a chassis 22. The diaper 20 and chassis 22 shown in FIG. 1 have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements that gather the material in the front and/or back waist region 36, 38 about the waist of the wearer to provide improved fit and containment. The crotch region 37 is that portion of the diaper 20 which, when the diaper 20 is worn, is generally positioned between the legs of the wearer.

The outer periphery of the chassis 22 is defined by longitudinal side edges 12 and end edges 14. The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing end edges 14 that are oriented generally parallel to the lateral centerline 110.

The chassis 22 may comprises a liquid permeable topsheet 24 having longitudinal side edges 25, a backsheet 26, and an absorbent core 28 between the topsheet 24 and the backsheet 26. The absorbent core 28 may have a body-facing surface and a garment facing-surface. The topsheet 24, the backsheet 26, and the absorbent core 28 may be assembled in a variety of well-known configurations. For example, the topsheet 24 may be joined to the core 28 and/or the backsheet 26. The backsheet 26 may be joined to the core 28 and/or the topsheet 24. It should be recognized that other structures, elements, or substrates may also be positioned in a joined or unjoined relationship between the core 28, the topsheet 24 and/or the backsheet 26. Nonlimiting examples of suitable diaper configurations are described generally in U.S. Pat. Nos. 3,860,003; 4,808,178; 4,909,803; 5,151,092; 5,221,274; 5,554,145; 5,569,234; 5,580,411; and 6,004,306 and U.S. application Ser. No. 11/055,743, which was filed Feb. 10, 2005.

The topsheet 24 typically includes a portion of the diaper 20 that is positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers, or a combination of natural and synthetic fibers. Generally, at least a portion of the topsheet 24 is liquid pervious, permitting liquid to readily penetrate through the thickness of the topsheet 24. Any portion of the topsheet 24 may be coated with a lotion as is known in the art. Examples of suitable lotions include those described in U.S. Pat. Nos. 5,607,760; 5,609,587; 5,635,191; and 5,643,588.

The absorbent core 28 may comprise a wide variety of liquid-absorbent materials commonly used in disposable diapers and other absorbent articles, such as, for example SAP particles and/or airfelt. These materials may be combined to provide a core 28 in the form of one or more layers, which may include fluid handling layers such as acquisition layers, distribution layers and storage layers. Such absorbent cores 28 may also include layers to stabilize other core components. Such layers may include a core cover and a dusting layer. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222 and in published U.S. patent application Ser. Nos. 04/0162536 and 04/0167486.

The SAPs useful in the present invention include a variety of water-insoluble, but water-swellable polymers capable of absorbing relatively large quantities of fluids. Such polymers materials are generally known in the art and include all those well-known polymers used or deemed useful in the context of disposable absorbent article technology. Particularly the SAPs disclosed in EP-A-752 892 or those disclosed in a textbook entitled "Modern Super Absorbent Technology" by F. L. Buchholz and A. T. Graham, published by Wiley VCH, New York, 1998 are useful in the context of the present invention. The SAP suitable for use with the present invention may be of one type (i.e., homogeneous) or mixtures of polymers. The SAPs may have a size, shape, and/or morphology varying over a wide range. When the SAP is in the form of particles, the particles generally do not have a large ratio of greatest dimension to smallest dimension. Suitable particle sizes and methods for determining particle sizes of the SAP particles are described in U.S. Pat. No. 5,061,259.

Additionally, the various layers of the core 28 described above, if present, may be joined to themselves and/or each other, such as, for example joining the cover layer to itself and/or to the dusting layer. By joining the core cover and/or the dusting layer in such a manner, the core 28 may be substantially encapsulated, thereby forming a core package. In other embodiments, the core may include a covering material that substantially envelopes the core to form a core package. The core package may include one or more "end seals" and/or one or more "side seals." End seal refers to a portion of the core package where the core cover and/or the dusting layer are joined to form an edge that is generally parallel to the lateral centerline 110 of the diaper 20. Side seal refers to a portion of the core package where the core cover and/or the dusting layer are joined to form an edge that is generally parallel to the longitudinal centerline 100 of the diaper 20. The end seal(s) and/or side seal(s) may be formed from one or more continuous bonds, but need not necessarily be so. Examples of end seals and side seals suitable for use with the present invention may be found in U.S. Publication No. 20060155254; U.S. Publication No. 20060155253A1; U.S. Pat. No. 7,013,941; and U.S. patent application Ser. No. 11/512,773, filed on Aug. 30, 2006, by Shunketsu, et al.

The backsheet 26 may be positioned such that it includes at least a portion of the garment-facing surface 120 of the diaper 20. The backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Other suitable backsheet 26 materials may include breathable materials that permit vapors to escape from the diaper 20 while still preventing exudates from passing through the backsheet 26. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

The backsheet 26 may also include more than one layer, as illustrated in the cut-away of FIG. 1. The backsheet 26 may include an outer cover 26a and an inner layer 26b that is at least partially disposed under the outer cover 26a, when viewed from the garment facing side of the diaper 20. The outer cover 26a may have longitudinal side edges 27a, and the inner layer 26b may have longitudinal side edges 27b. The outer cover 26a may be made of a soft, non-woven material. The inner layer 26b may be made of a substantially water-impermeable film. The outer cover 26a and an inner layer 26b may be joined together by adhesive or any other suitable material or method. In addition, the outer cover 26a and/or the inner cover 26b may also each include more than one layer of material, such as, for example in a laminate structure.

The diaper 20 may also include a fastening system 50. When fastened, the fastening system 50 typically interconnects the front waist region 36 and the rear waist region 38 resulting in a waist circumference that generally encircles a wearer of the diaper 20. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 shows a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

Figure 2:
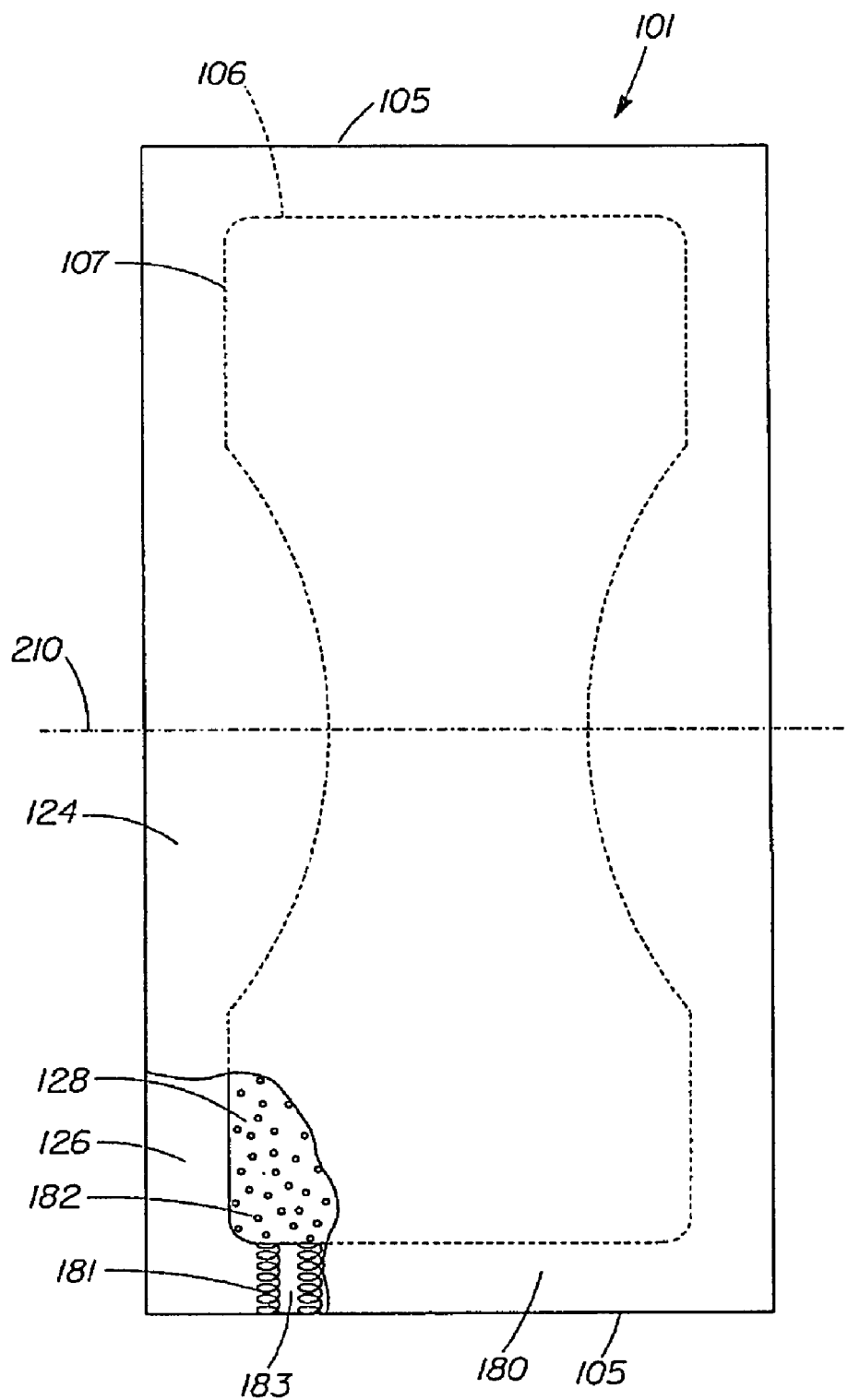
FIG. 2 is a plan view of a disposable absorbent article in a flat, uncontracted state.

FIG. 2 shows a partially cutaway view of a diaper 101 having an endflap seal 180 according to one example of an embodiment of the present invention. The diaper 101 shown in FIG. 2 has two opposing end edges 105 generally parallel to the transverse centerline 210, a topsheet 124, and backsheet 126 configured in an overlying relationship. A portion of the topsheet 124 may be joined with a portion of the backsheet 126 in the vicinity of one or both of the opposing end edges 105 to form one or more endflap seals 180. The topsheet 124 and the backsheet 126 may be joined together with a spiral patterned SBS/SIS adhesive 181. The endflap seal 180 may include some or all of the area that lies between the end seal 106 of the core 128 and the end edge 105 of the diaper 101. The endflap seal 180 may help prevent the loss of material disposed in the vicinity of the absorbent core 128, such as, for example SAP particles 182. It may be desirable, however, to configure the endflap seals(s) 180 to permit the escape of air that may be trapped in the diaper 101, such as, for example by including channels 183. By providing an endflap seal 180 that may prevent or at least inhibit the escape of some, if not all, of the SAP particles 182 in the diaper 101, the likelihood of a gel on skin occurrence may be reduced.

As noted above, an adhesive may be used to join one or more components of a disposable absorbent article to themselves or to one another during the construction process. Nonlimiting examples of such joinder using an adhesive include, but are not limited to core cover to dusting layer sealing (e.g., to provide a side seal 107 or an end seal 106), topsheet 24, 124 to backsheet 26, 126 (e.g., endflap seal 180), backsheet 26, 126 to dusting layer, backsheet 26, 126 to core 28, 128, elastic member 64 to nonwoven and/or film to form a barrier cuff 60 or a gasketing cuff 70, backsheet outer cover 26a to backsheet inner layer 26b to form a backsheet 26, barrier cuff 60 to backsheet 26, barrier cuff 60 to topsheet 24, receiving member 54 to topsheet 24, ear 40, 42 to backsheet 26. Due to the number of components that may be used to construct a typical diaper 20 and the variety of ways in which the components may be joined, it may be desirable to provide an adhesive with physical properties suitable for a variety uses related to disposable absorbent article construction.

One characteristic of an adhesive that may be of particular importance is the bond strength provided by the adhesive. When an adhesive provides a suitably strong bond between joined absorbent article components, the likelihood of a component failure, such as, for example the failure of the endflap seal 180, may be decreased, and thus the likelihood of SAP particles escaping from the absorbent article and causing a gel on skin occurrence may be prevented or at least reduced.

It is commonly known that unswollen or partially swollen SAP particle(s) may be found in the proximity of the bonded portion(s) of the endflap seal 180 (e.g., lodged between the topsheet 124 and the backsheet 126 near an adhesive bond). Without being limited by theory, it is believed that such SAP particles, when exposed to an aqueous fluid, will swell and may exert a separating force on the endflap seal 180. If the separating force is greater than the bond strength of the adhesive, the endflap seal 180 may separate or partially separate, possibly resulting in the escape of SAP particles from the diaper 20, 101. Any increase in the likelihood of SAP particles escaping from the diaper 101 may in turn lead to an undesirable increase in the chance of a gel on skin occurrence. Thus, it may be advantageous to provide an endflap seal 180 having an adhesive bond strength that is equal to or greater than the force exerted by swelling SAP particle(s).

In the past, styrene-isoprene-styrene block copolymer adhesives ("SIS adhesives") were commonly used as construction adhesives in disposable absorbent articles. However, some manufacturers found that due to a limited supply and increasing demand for isoprene (a component of SIS adhesives) the cost of using SIS adhesives for the commercial manufacture of disposable absorbent articles may rise to an undesirable level. Some manufacturers of disposable absorbent articles also found that SIS adhesives may produce an odor(s), which consumers find undesirable when the consumer detects the odor.

In an effort to find alternative adhesives, some manufacturers investigated the possibility of replacing SIS adhesives with styrene-butadiene-styrene block copolymer adhesives ("SBS adhesives"). However, the SBS adhesives, while typically cheaper and more readily available, may not deliver the performance results, such as, for example sufficient bond strength, desired by manufacturers and consumers of disposable absorbent articles. Some manufacturers have also found that SBS adhesives may behave poorly under certain manufacturing conditions. For example, some SBS adhesives may build up on the nozzles of the applicators that apply the adhesive to the absorbent article. The build-up of adhesives on the nozzles may undesirably alter the performance of the nozzles. In addition or alternatively, the adhesive may build up on the nozzles to a particular amount and then drop onto the absorbent article substrate resulting in the formation of undesirable blobs of adhesive on the substrate or the manufacturing equipment. Examples of SBS adhesives are described in more detail in U.S. Pat. No. 6,232,391, issued to Sambasivam, et al., May 15, 2001, and U.S. Pat. No. 4,526,577, issued to Schmidt, et al., Jul. 2, 1985, which are incorporated herein by reference.

Surprisingly, it has been found that an SBS based adhesive that also includes an amount of SIS adhesive (together an "SBS/SIS adhesive") may overcome at least some of the undesirable characteristics described above. As used herein, the term "SBS based adhesive" refers to an adhesive that includes more than 50 weight % of an SBS block copolymer adhesive, based on the weight of the SBS/SIS adhesive. Suitable examples of SBS/SIS adhesives for use with the present invention include SBS/SIS adhesives having less than 50 weight %, but more than 0.1% by weight of the SBS/SIS adhesive of an SIS adhesive. Other suitable examples include SBS/SIS adhesives with less than 25 weight %; less than 15 weight %; less than 10 weight %, but more than 0.1% by weight of the SBS/SIS adhesive of an SIS adhesive. One particularly suitable example of an SBS/SIS adhesive for use in accordance with the present invention is DM526 available from the National Starch & Chemical Company, Bridgewater, N.J. 08807.

Table 1 below shows a comparative analysis of the bond strengths of an SBS adhesive, an SIS adhesive, and an SBS/SIS adhesive. The three adhesive samples were obtained from commercially available sources and were each used to construct an endflap seal on different diapers. The endflap seal of each different diaper was subjected to the Shear Hang Time Test described hereinbelow to measure the adhesive bond strengths. Five diapers were constructed with the SBS adhesive and tested, ten diapers were constructed with the SIS adhesive and tested, and ten diapers were constructed with the SBS/SIS adhesive and tested. The individual measurements were averaged and the averages are recorded below. The SBS adhesive tested is available from the National Starch & Chemical Company, Bridgewater, N.J. 08807 as product number DM426N. The SIS adhesive tested is available from the H.B. Fuller Company, St. Paul, Minn. as product number 1358LO. The SBS/SIS adhesive tested is available from the National Starch & Chemical Company, Bridgewater, N.J. 08807 as product number DM526.

TABLE 1

| Sample | Shear Hang Time (sec.) |
| --- | --- |
| SBS adhesive | 67 |
| SIS adhesive | 340 |
| SBS/SIS adhesive | 520 |

Figure 3:
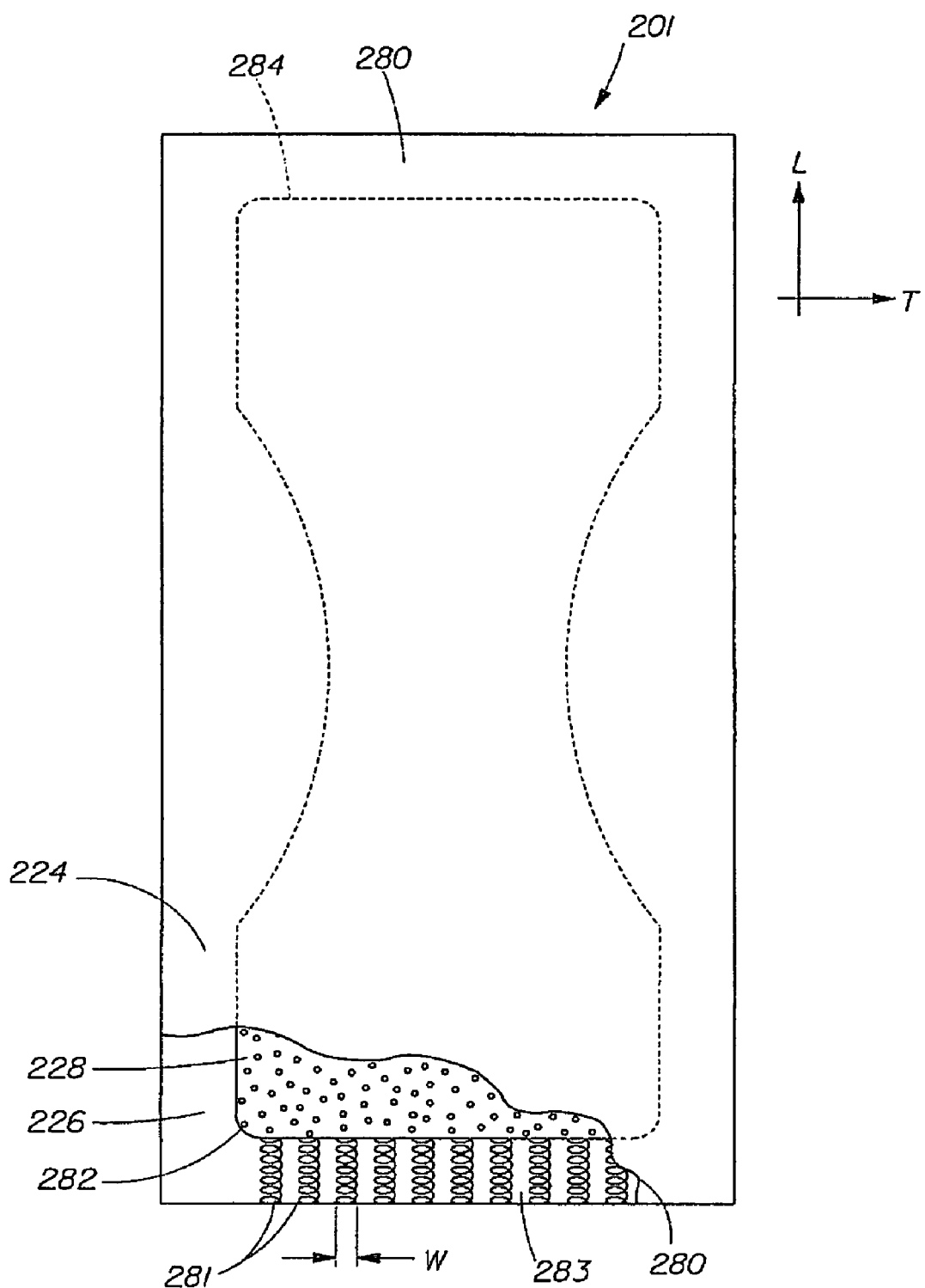
FIG. 3 is a plan view of a disposable absorbent article in a flat, uncontracted state.

In addition to the adequate bond strength discussed above, it is believed, without being limited by theory, that the pattern in which the adhesive is applied to a disposable absorbent article may also impact the likelihood of a gel on skin occurrence. FIG. 3 shows a partial cutaway view of a disposable absorbent article 201 according to one example of an embodiment of the present invention. The disposable absorbent article 201 shown in FIG. 3 may include a backsheet 226 and a topsheet 224 in an overlying relationship, an absorbent core 228 positioned between the topsheet 224 and backsheet 226, and an endflap seal 280 formed by joining the topsheet 224 to the backsheet 226 with a spiral patterned adhesive 281. The disposable absorbent article 201 also has a longitudinal direction L and a transverse direction T, which is substantially perpendicular to the longitudinal direction L. The spiral patterned adhesive 281 may be applied to the topsheet 224 and/or the backsheet 226, such that one or more channels 283 are formed between the spiral patterned adhesive 281. The channels may be configured to allow the passage of air, but inhibit or prevent the escape of SAP particles 282 disposed in the absorbent core 228. The spiral patterned adhesive 281 has a width W and may be applied by any suitable means commonly known in the art. In one embodiment of the present invention, the SBS/SIS adhesive may be applied with one or more spray-on nozzles. Spray-on adhesive systems known to those skilled in the art typically use pressure to force a material through a nozzle. Suitable nozzle sizes for use with the present invention include nozzles having an inner diameter of between about 380 μm and about 510 μm.

Figure 4:
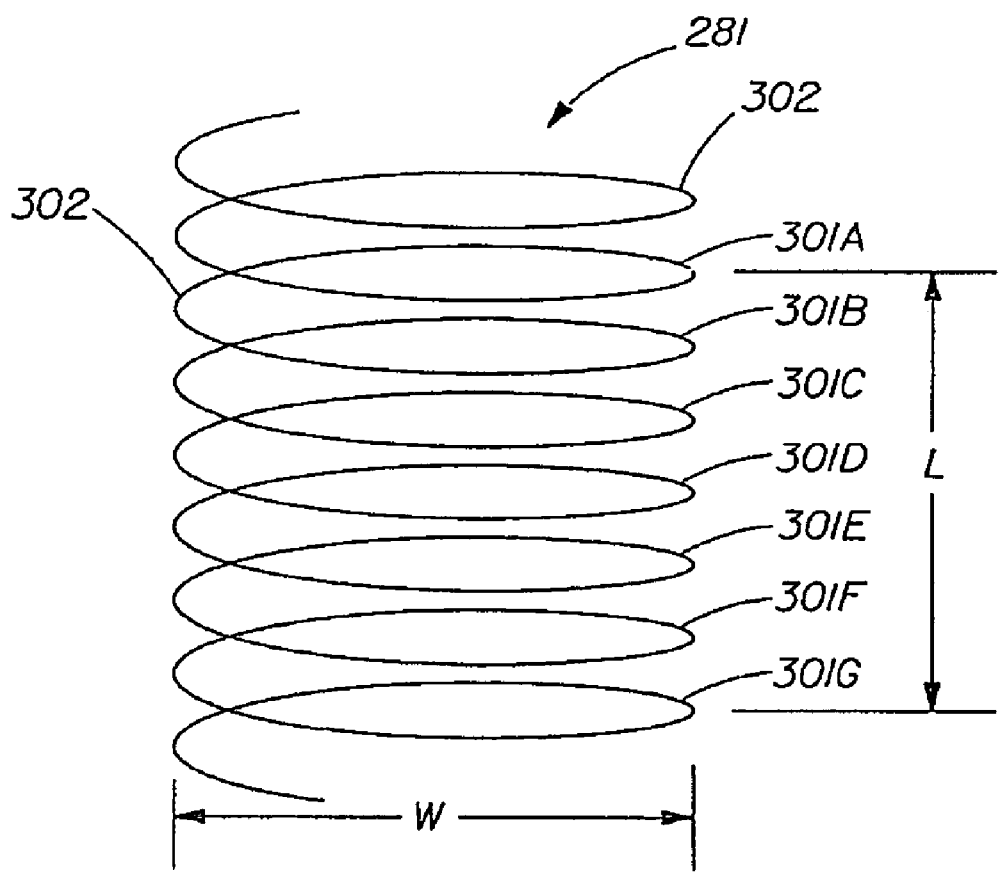
FIG. 4 is an example of an idealized spiral pattern.

In at least one embodiment of the present invention, the SBS/SIS adhesive used to bond an endflap seal 280 may be applied in a spiral pattern with a spiral frequency of from 1 to 10 spirals per 2.54 cm. Alternatively, the spiral pattern may have a spiral frequency of from 3 to 6 spirals per 2.54 cm. Spiral frequency is determined by counting the number of crossover points encompassed by 2.54 cm of the spiral pattern in the longitudinal direction and subtracting one. When determining spiral frequency, only the crossover points on one side of the spiral pattern are counted. FIG. 4 shows a magnified view of the spiral patterned adhesive 281 shown in FIG. 3. It is to be understood that the spiral patterned adhesive 281 shown in FIG. 4 is an idealized spiral pattern, and that the present invention contemplates other patterns or shapes generally resembling one or more spirals, which may not necessarily include idealized spirals. For example, some spiral patterned adhesives 281 according to the present invention may have one or more portions that are wider than one or more other portions. In other examples, one or more portions of the spiral patterned adhesive 281 may have a different spiral frequency than one or more other portions of the spiral patterned adhesive 281. The spiral patterned adhesive 281 has a length L and two outer edges 302. In this example, the length L equals 2.54 cm. It is to be understood that while the length L may include the entire length of the spiral pattern, it need not (and in this particular example does not) necessarily do so. Instead, the length L is used to help determine the spiral frequency, as will be seen. For purposes of determining spiral frequency, the spiral patterned adhesive 281 has seven crossover points 301A, 301B, 301C, 301D, 301E, 301F, and 301G encompassed by the length L. As used herein, "crossover point" refers to a point in the spiral patterned adhesive 281 where the curvilinear lines of the spiral pattern intersect at an outer edge 302 of the spiral patterned adhesive 281. Thus according to the method of determining spiral frequency stated above, the spiral patterned adhesive 281 shown in FIG. 4 has a spiral frequency of 6 spirals per 2.54 cm (7 crossover points minus one).

The spiral patterned adhesive 281 also has a width W. It is believed, without being limited by theory, that the width W of the spiral patterned adhesive 281 may impact the performance characteristics of the endflap seal 280. For example, if the width W of the spiral patterned adhesive 281 is too narrow for a given spiral density, the channels formed between areas of spiral patterned adhesive 281 may be too wide, and thus the likelihood of SAP particles escaping through the endflap seal 280 may increase. On the other hand, if the spiral patterned adhesive 281 is too wide for a given spiral density, the channels formed between areas of spiral patterned adhesive 281 may be too narrow to provide an escape route for air that may be trapped in the absorbent article, and thus potentially increase the likelihood of an end flap seal 280 failure. As used herein, "spiral density" refers to the number of spiral patterned adhesive 281 in the endflap zone area 280, as counted in the transverse direction T. For example, the endflap seal 280 shown in FIG. 3 has a spiral density of 6. In one particular embodiment of the present invention, the endflap seal 280 may include the spiral patterned adhesive 281 in a spiral density of between about 5 and 8 and the spiral patterned adhesive 281 having a width of between about 5 mm and 25 mm or even between about 10 mm and 20 mm.

While the examples shown in the figures may depict the spiral patterned adhesive 281 as being disposed only in the area of the endflap seal 280, it is to be understood that the one or more adhesive spirals 281 need not necessarily be limited to such area, but may be part of one or more continuous or noncontinuous adhesive spirals that traverse part of or even the entire longitudinal L length of the disposable absorbent article 201. In addition, the spiral patterned adhesive 281 need not necessarily be disposed in the longitudinal direction L of the disposable absorbent article 201, but may be disposed in any direction that is generally orthogonal to the end edge 284 of the core 228.

Table 2 below shows the various endflap seal bond strengths for four disposable diaper products. The bond strengths were measured according to the Shear Hang Time Test. Product 1 is a size 4 PAMPERS BABY DRY brand disposable diaper, available from the Procter & Gamble Company, Cincinnati, Ohio. Product 1 includes an endflap seal constructed with a spiral patterned SBS/SIS adhesive, in accordance with the present invention. The spiral patterned adhesive was applied to between 50% and 90% of the total endflap seal area. Product 2 is a size 6 HUGGIES brand disposable diaper manufactured by the Kimberly-Clark Corporation, Neenah, Wis. Product two includes an endflap seal that appeared to be constructed with a commonly known adhesive applied in a spiral pattern over an area of between 50% and 90% of the total endflap seal area. Product 3 is a size 4 HUGGIES SUPREME brand disposable diaper manufactured by the Kimberly-Clark Corporation, Neenah, Wis. Product 3 includes an endflap seal that appeared to be constructed with a commonly known adhesive applied over substantially the entire endflap seal area. Product 4 is a WHITE CLOUD brand disposable diaper manufactured by Tyco Healthcare Retail Services AG, Schaffhausen, Switzerland. Product 4 includes an endflap seal that appeared to be constructed with a commonly known adhesive applied over substantially the entire endflap seal area.

Three samples of each product were tested. The shear hang time results for each sample were measured and averaged. Both the individual results and the average of the three measurements are shown in Table 2. In addition, the shear hang times were adjusted to account for differences in glue length (i.e., to account for any difference that might be present due to the length of the glue as opposed to the strength of the bond), and recorded as SHT/MD Length (min./mm) in the last column of Table 2.

The length of the adhesive in the machine direction (i.e., the longitudinal distance between the end of the core or the end seal of the core package and the end edge of the diaper that includes adhesive) was measured and recorded for each product sample. The free space (i.e., the area of the endflap seal not covered by adhesive) was determined by subtracting the calculated area covered by adhesive from the total area of the endflap seal area. The total area of an endflap seal was determined by calculating the area from the end edge of the core to the closest end edge of the diaper between the side edges of the core. The area covered by adhesive was calculated by multiplying the length of the adhesive pattern by the width of the adhesive pattern. For spiral patterned adhesive, the width of the adhesive pattern was determined by measuring the width of the spiral pattern at the widest point. While Table 2 shows examples of endflap seals having between 10% and 50% free space, it is to be understood that embodiments where the endflap seal has greater than 50% free space are also contemplated by the present invention. In some embodiments of the present invention, the free space may be about equal to the area comprised by the channels.

TABLE 2

|  | Endbonding Pattern | Adhesive length in MD | Free Space (%) | SHT (Min.) | | | SHT Ave. (min) | SHT/MD Length (min./mm) |
|---|---|---|---|---|---|---|---|---|
| Product 1 | Spiral | (22 + 25 + 23)/3 = 23.3 mm | Between 10%–50% | 37 | 45 | 18.7 | 33.4 | 1.4 |
| Product 2 | Spiral | (33 + 34 + 35)/3 = 34 mm | Between 10%–50% | 0.7 | 0.2 | 0.1 | 0.3 | 0.01 |
| Product 3 | Meltblown | (29 + 29 + 30)/3 = 29.3 mm | 0% | 2.4 | 1.4 | 1.5 | 1.8 | 0.1 |
| Product 4 | Comb-Shim + Elastomer layer + Spiral | (23 + 28 + 26)/3 = 25.7 mm | 0% | 6.7 | 24.3 | 17.2 | 16.1 | 0.6 |

As can be seen from the data in Table 2, the average Shear Hang Time for Product 1 is about two times greater than that of the next highest average shear hang time. While the data in Table 2 may show SHT values for Product 1 that are greater than 18 minutes, it is to be understood that shear hang time values of ☐40 seconds when the free space is less than 100% are contemplated by the present invention. The present invention also contemplates embodiments wherein the free space may be less than about 75%; less than about 50%; or even less than about 30% of the endflap seal area and the endflap seal bond strength may be, for example, greater than about 100 seconds; greater than 200 seconds; greater than about 500 seconds; or even greater than about 1000 seconds.

In embodiments of the present invention where it is desirable to use an SBS/SIS adhesive to join components of disposable absorbent articles to themselves or to one another, the bond strength may be defined by the Peel Force test, which is disclosed in the Test Methods section hereinbelow. One nonlimiting example of such an embodiment includes a polymeric backsheet film adhesively joined to a nonwoven backsheet outer cover with an SBS/SIS adhesive, such that an adhesive bond having a Peel Force of greater than about 0.4 N/cm; greater than about 0.5 N/cm; or even greater than about 0.9 N/cm is provided. Another nonlimiting example includes a core cover adhesively joined to itself and/or to a dusting layer with an SBS/SIS adhesive to form a side seal such that an adhesive bond having a Peel Force of greater than about 4 N; greater than about 6 N; or even greater than about 7 N is provided. Alternatively, the dusting layer may be joined to itself and/or to a core cover with an SBS/SIS adhesive to form a side seal.

In addition to providing the bond strength described above, it has been found that a disposable absorbent article made with an SBS/SIS adhesive may also produce less undesirable odor. It is commonly known that at least some adhesives used in the making of disposable absorbent articles may produce odors that consumers of disposable absorbent articles find undesirable. When an odor has a rating of greater than 3.0, as measured according to the Odor Sensory Test, test subjects will typically report the detection of an odor. As the odor level increases, for example to 6.0 or even 8.0, test subjects often report the odor as increasing in both detectability and undesirability. An SBS/SIS adhesive or a disposable absorbent articles constructed with an SBS/SIS adhesive according to the present invention may have odor ratings at or below 8.0; at or below 6.0; or even at or below 3.0, when measured according to the Odor Sensory Test.

Test Methods

Shear Hang Time Test.

Figure 5:
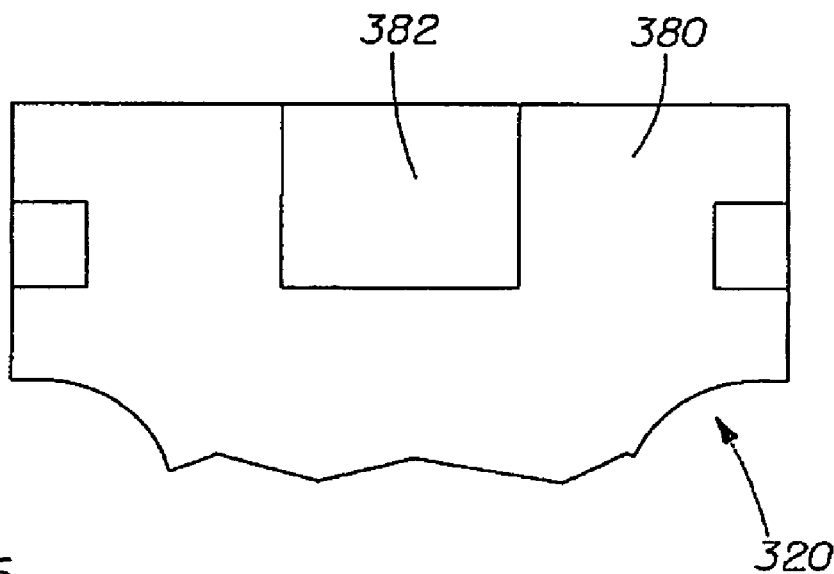
FIG. 5 is a partial plan view of a disposable absorbent article.
Figure 6:
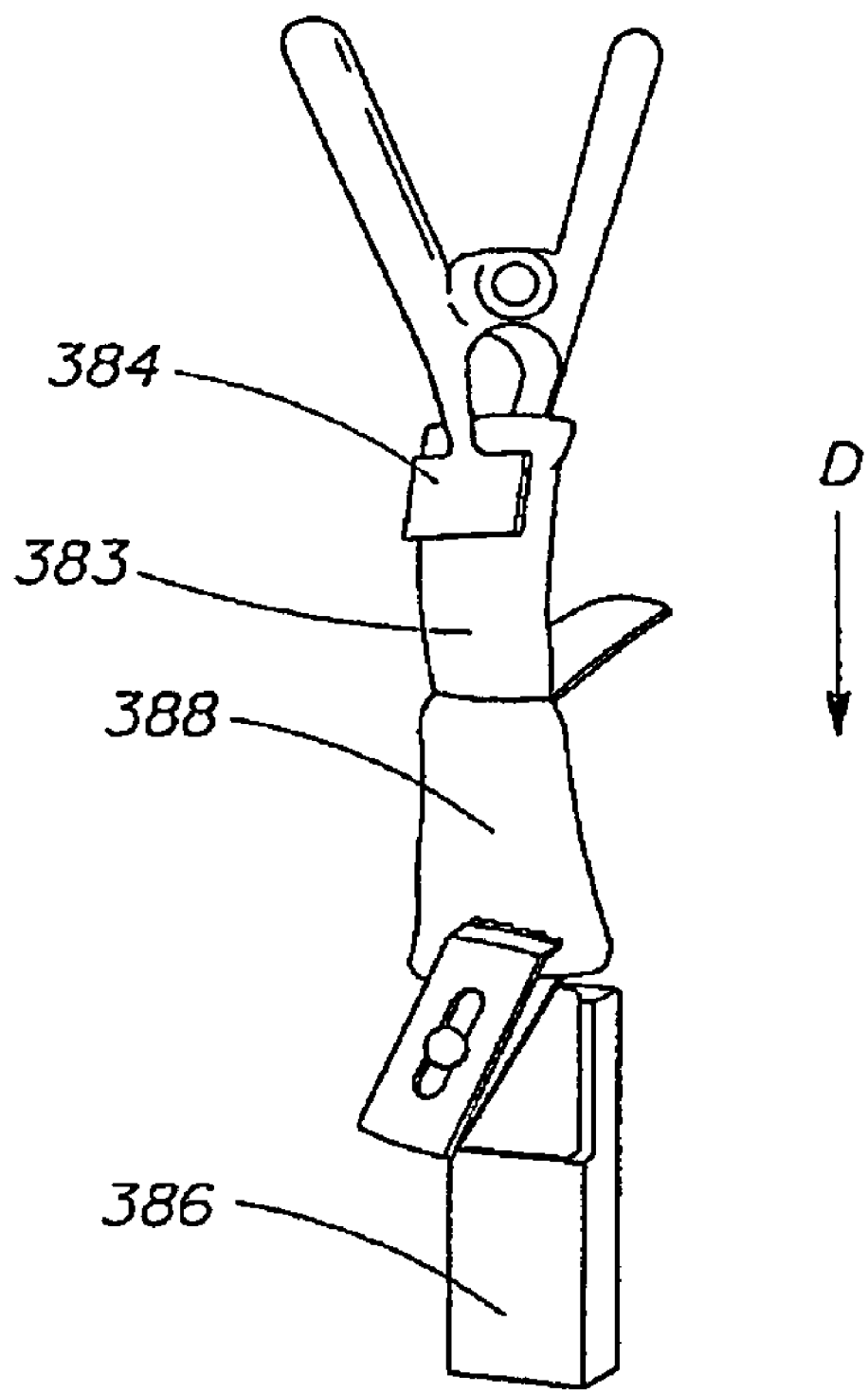
FIG. 6 is a partial view of the Shear Hang Time Test setup.

The Shear Hang Time Test method is used to determine the bond strength of the endflap seal of a diaper.
Equipment:
Scissors
Hunter Force gauge
Timer
Metal Ruler traceable to NIST, DIN, JIS or other comparable National Standard, graduated in mm, longer than the length to be measured.
300 g weight with clamp (for Medium to Extra Large sizes).
200 g weight with clamp (for Newborn and Small sizes).
Procedure Open up the diaper 320. From the shorter endflap seal 380 of the diaper 320 cut out a 40 mm wide×50 mm long strip 382 from the center of the diaper 320 as shown in FIG. 5. If there are none or only weak chassis glue beads/spirals present, the weakest part of the endflap seal 380 is to be used as the test strip 382. Fold out the test strip 382 like a book and carefully remove the core material. Clamp the polymeric film side 383 of the test strip 382 into the jaw 388 of the Hunter gauge as shown in FIG. 6. Attach the appropriate weight 386 to the other side 384 of the test strip 382 and lower slowly until the weight hangs freely on the test strip 382 in the downward direction D. Start the timer as soon as the weight 386 hangs freely in the downward direction D. Stop the timer immediately after the weight 386 has fallen off. Report the determined value(s) to the nearest 1 second. Repeat the test on 10 samples and record the individual bond strengths. Average the individual bond strengths and report the average value as Shear Hang Time.

Peel Force Test

This method measures the force required to separate the laminate structure, (e.g., nonwoven from the poly film) of a disposable absorbent article. The laminate is peeled using a constant rate of extension tensile tester and the average load in N/cm is calculated. In order to more easily describe the test method, the laminate backsheet of a finished disposable diaper product is exemplified. However, one of ordinary skill in the art will appreciate that this test may be readily adapted to measure the force required to separate other laminate structures or joined components that may be included in a disposable absorbent article.

Equipment
Tensile Tester: Universal constant rate of extension tensile testing machine with computer interface.
Jaws: Both upper and lower jaws: (2) 2.54 cm×2.54 cm flat rubber face clamps
Load Cell: Chosen so that force results for the samples tested will be between 10% and 90% of the capacity of the load cell
Precision Cutter: 2.54 cm wide precision cutter, Thwing-Albert Instruments Co., Philadelphia, Pa. or equivalent
Scissors
Equipment Settings
1. Choose a load cell so that force results for the samples tested will be between 10% and 90% of the capacity of the load cell or load range used.
2. Calibrate the tensile tester according to manufacturer's instructions or SOP before beginning any testing.
3. Set the gage length to 2.54 cm. With the flat clamps, gage length should be calculated from the bottom of the top clamp to the top of the bottom clamp.
4. Set the crosshead speed to 30.5 cm/min.
5. Set crosshead travel at 19.5 cm.
6. Set peel start at 1.5 cm.
7. Set the peel endpoint at 18 cm. This endpoint can be adjusted (i.e., a "movable marker"), to accommodate peels shorter than the 18 cm.
8. Set the tensile program to calculate the average force in (N) between the peel start and endpoint.
Sample Preparation
1. Using the precision cutter, cut a 2.54 cm strip of the disposable absorbent article in the cross direction. If the disposable absorbent article is a diaper cut the strip approximately 1.0 cm below the landing zone. Using scissors, cut the test strip in the machine direction at the center line of the material to give two samples of equal length.
2. Remove the back-sheet from the absorptive body and topsheet.
3. Manually separate the 2 layers of the backsheet for a distance of approximately 2.54 cm in the test direction, taking care not to tear either layer.
4. If the peel can not be started, record bond strength as "total bond."
Procedure
1. Perform testing in a conditioned room maintained at 23°±2° C. and 50%±2% relative humidity.
2. Before loading each specimen, zero the instrument according to manufacturer's instructions.
3. Insert the nonwoven layer of the specimen into the upper jaw and close the jaw. Align the specimen between the lower and upper jaws. Insert the poly layer of the specimen into the lower jaw and close the jaw with enough tension to eliminate any slack, but less than 0.05 N of force on the load cell.

Note: Do not zero the instrument after the specimen has been loaded.

4. Start the tensile tester and data collection device simultaneously as described by the manufacturer's instructions.
5. Remove the specimen from the clamps and return the crosshead to the starting position in preparation for the next specimen.
6. If the peel is complete before the default 18 cm, manually adjust the peel endpoint to the extension at which the peel ends.
7. If specimen tears during the first 5.0 cm of testing, record the bond strength as "total bond".
8. Repeat the test on 10 samples, record the individual bond strengths. Average the individual bond strengths and report the average value as Peel Strength.

Calculations

Set the test software to calculate the Average Peel Force in (N) between the peel start and peel endpoint.

Laminate Bond Strength (N/cm)=Average Peel Force (N)/Specimen Width (cm).

Reporting

If peel can not be started on the specimen, report as "total bond".

If specimen can not be peeled further than 5 cm extension, report as "total bond".

Odor Sensory Test

The purpose of this test is to evaluate odor that may be associated with adhesives used in absorbent articles on a scale of 0 to 10, where 0 is "no smell" and 10 is an "extremely strong smell."

Equipment

An appropriate number of 15.25 cm×15.25 cm polyester based film sheets with a thickness of approximately 508 μm. (e.g., MYLAR film, available from DuPont, Wilmington, Del.).

Procedures

A. General

1. All panelists are screened for odor competency sensitivity and should be able to differentiate between odors. A fragrance screener consisting of sets of three different laundry detergents is given to the panelists. The panelists are asked to tell us which one is different when evaluating three samples in a set. Panelists are calibrated prior to each test using references and re-screened each year.
2. Panelists must be able to perceive odors. They will be excluded from the test for colds, allergies, etc. Panelists should avoid coffee, spicy foods, heavy cologne, etc. Non-smoking panelists are preferred.
3. Testing should be performed in an open room suitable for performing an odor sensory test (e.g., a room that is not used for chemical storage and has a relatively high rate of air turnover), however, the test should not be performed in a fume hood or similar device.

B. Sample Preparation—

Evenly apply approximately 100 mg of adhesive to be tested over a 2.54 cm×15.25 cm strip on a film sheet. Place a second sheet over the first, such that the adhesive is sandwiched between the two film sheets. If it is necessary to melt the adhesive prior to application to the film sheet, the adhesive temperature should be kept within the manufacturer recommended application temperature and should be applied to the film as soon as it is melted. Avoid a long residence time in a holding tank. The compression pressure to laminate the two film sheets together may be what is available on the particular equipment being used to prepare the samples.

C. Sensory Evaluation—To be Performed at Least Twice in the Same Week.

1. Prior to any evaluation, panelists are instructed on the nature of the test and calibrated. Calibration involves instructing panelists to sniff one Control of "0," which is an empty glass jar, and one control from the samples to be tested in the range of 4-8, as determined by odor experts. Odor experts are consumer panelists who have been qualified for rating odor levels using standard samples.
2. 25 Panelists are each given a sample and instructed to peel the film sheets apart and sniff the adhesive sample.
3. Panelists may sniff more than once. Panelists are limited to no more than 10-12 samples per session so as to not fatigue their olfactory capability. Panelists are asked to allow approximately one minute between sniffing samples.
4. Panelists provide a sensory grade of the odor on a scale of 0 to 10, where 0 is "no smell" and 10 is an "extremely strong smell."
5. The odor sensory scores from the 25 panelists are recorded and averaged. The average odor level score is reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a pair of opposing end edges and a pair of longitudinal side edges, the absorbent article comprising:
   a. a topsheet, a backsheet and an absorbent core disposed between the topsheet and backsheet, the absorbent core comprising particles of superabsorbent polymer;
   b. a spiral patterned SBS/SIS adhesive disposed on a portion of the disposable absorbent article at a spiral density of between 5 and 8 and a spiral width of between 5 and 25 mm, the adhesive joining a portion of the topsheet to a portion of the backsheet by an adhesive bond to form an endflap seal, the adhesive bond having a shear hang time of greater than 40 seconds as measured according to the Shear Hang Time Test; and
   c. at least one channel for permitting the escape of air from inside the article to an external environment but substantially preventing the escape of the superabsorbent polymer particles to the external environment, the channel being disposed between two spirals.

2. The disposable absorbent article of claim 1, wherein the adhesive bond has a peel force of greater than 4.0 N as measured according to the Peel Force test.

3. The disposable absorbent article of claim 1, wherein the spiral patterned adhesive has a frequency of from 1 to 10 spirals per 2.54 cm.

4. The disposable absorbent article of claim 1, wherein the spiral patterned adhesive has a frequency of from 3 to 6 spirals per 2.54 cm.

5. The disposable absorbent article of claim 1, wherein the SBS/SIS adhesive comprises less than 15 weight % by weight of the SBS/SIS adhesive of an SIS adhesive.

6. The disposable absorbent article of claim 1, wherein the adhesive bond has a shear hang time of greater than about 100 seconds.

7. The disposable absorbent article of claim 1, further comprising an odor rating of less than or equal to 8.0 as measured according to the Odor Sensory Test.

8. The disposable absorbent article of claim 1, wherein the backsheet includes a nonwoven layer adhesively bonded to a polymeric film layer by the adhesive, the adhesive bond having a Peel Force value of greater than about 0.4 N/cm.

9. The disposable absorbent article of claim 1, wherein the absorbent core is configured as a core package, the core package comprising a side seal.

10. The disposable absorbent article of claim 1, wherein the area comprising the endflap seal includes more than about 10% free space.

11. A process for forming an endseal on a disposable absorbent article, the process comprising the steps of:
   a. providing a topsheet material having a first pair of opposed transverse end regions, a backsheet material having a second pair of opposed transverse end regions, and an absorbent core configured to be positioned between the topsheet material and the backsheet material, the absorbent core comprising particles of superabsorbent polymer;
   b. applying an SBS/SIS adhesive to the first and/or second pair of transverse end regions in a spiral pattern at a spiral density of between 5 and 8 and a spiral width of between 5 and 25 mm; and
   c. adhesively bonding one or more portions of the first pair of transverse ends to one or more portions of the second pair of transverse ends with the adhesive such that the resulting joined portions form at least one endflap seal including one or more channels for permitting the escape of air from inside the article to an external environment and substantially preventing the escape of the superabsorbent polymer particles to the external environment, the channel being disposed between two spirals, the endflap seal having a shear hang time of greater than about 40 seconds as measured according to the Shear Hang Time Test.

12. The process of claim 11, wherein the spiral patterned adhesive has a frequency of from 1 to 10 spirals per 2.54 cm.

13. The process of claim 11, wherein the widest portion of the spiral patterned adhesive has a width of between about 5 mm and 25 mm.

14. A disposable absorbent article comprising:
   a. a topsheet, a backsheet and an absorbent core comprising particles of superabsorbent polymer disposed between the topsheet and backsheet;
   b. a covering material comprising at least one of a core cover and a dusting layer, the absorbent core being enveloped by the covering material to form a core package, the covering material being sealed along a seal line with an adhesive bond comprising an SBS/SIS adhesive to form a core package seal along at least one of the end edge(s) and side edge(s) of the core package; and
   c. the adhesive bond having a shear hang time of greater than about 40 seconds as measured according to the Shear Hang Time Test.

15. The disposable absorbent article of claim 14, wherein the adhesive bond is in an intermittent pattern along the seal line, the seat line comprising free space; the free space comprising one or more air passages from the core to an external environment.

* * * * *